US011045310B2

(12) United States Patent
Glick

(10) Patent No.: US 11,045,310 B2
(45) Date of Patent: Jun. 29, 2021

(54) MALE FORM AS AN ATTACHMENT ELEMENT FOR AN INJECTOR, AND INJECTOR FOR IMPLANTING AN INTRAOCULAR LENS IN AN EYE

(71) Applicant: Carl Zeiss Meditec Production, LLC, Ontario, CA (US)

(72) Inventor: Robert Glick, Trabuco Canyon, CA (US)

(73) Assignee: Carl Zeiss Meditec Production, LLC, Ontario, CA (US)

(*) Notice: Subject to any disclaimer, the term of this patent is extended or adjusted under 35 U.S.C. 154(b) by 177 days.

(21) Appl. No.: 15/835,725

(22) Filed: Dec. 8, 2017

(65) Prior Publication Data

US 2019/0175335 A1 Jun. 13, 2019

(51) Int. Cl.
*A61F 2/16* (2006.01)

(52) U.S. Cl.
CPC ............ *A61F 2/1662* (2013.01); *A61F 2/167* (2013.01); *A61F 2/1678* (2013.01); *A61F 2/1691* (2013.01); *A61F 2002/1681* (2013.01)

(58) Field of Classification Search
CPC ...... A61F 2/1662; A61F 2/1667; A61F 2/167; A61F 2/1672; A61F 2/1675; A61F 2/1691; A61F 2/1678; A61F 2/1664; A61B 2560/063
USPC ....................................................... 623/6.12
See application file for complete search history.

(56) References Cited

U.S. PATENT DOCUMENTS

| 4,215,701 A | * | 8/1980 | Raitto | ............... A61B 5/15003 |
| | | | | 600/576 |
| 5,499,987 A | * | 3/1996 | Feingold | ............... A61F 2/1664 |
| | | | | 606/107 |
| 6,162,229 A | * | 12/2000 | Feingold | ............... A61F 2/1664 |
| | | | | 606/107 |

(Continued)

FOREIGN PATENT DOCUMENTS

| CN | 101068507 A | 11/2007 |
| CN | 202288610 U | 7/2012 |

(Continued)

OTHER PUBLICATIONS

European Search Report issued in EP 18210252.5, which is a counterpart hereof, dated May 6, 2019.

(Continued)

*Primary Examiner* — Martin T Ton
(74) *Attorney, Agent, or Firm* — Falk Ewers; Ewers IP Law PLLC

(57) ABSTRACT

A male form is configured as an attachment element for an injector for implanting an intraocular lens in an eye. The male form includes an elongate carrier part and a front part that is arranged at one end of the elongate carrier part. The front part has a front side and is made of an elastically deformable material, the deformable material being compressible at least in the direction of a longitudinal axis (A) of the male form. The front side includes a first peripheral side, an opposite second peripheral side, and at least one elongate indentation, which is formed in the front part and which is open at the front side. The indentation extends between the two peripheral sides and opens out at the peripheral sides. An injector for implanting an intraocular lens having the male form is also disclosed.

10 Claims, 6 Drawing Sheets

(56) References Cited

U.S. PATENT DOCUMENTS

| | | | |
|---|---|---|---|
| 6,334,862 B1 | 1/2002 | Vidal et al. | |
| 6,733,507 B2 * | 5/2004 | McNicholas | A61F 2/1678 |
| | | | 606/107 |
| 6,923,815 B2 | 8/2005 | Brady et al. | |
| 8,246,631 B2 | 8/2012 | Pynson | |
| 2001/0020171 A1 | 9/2001 | Heyman et al. | |
| 2002/0193805 A1 | 12/2002 | Ott et al. | |
| 2008/0027461 A1 | 1/2008 | Vaquero et al. | |
| 2009/0292293 A1 | 11/2009 | Bogaert et al. | |
| 2016/0000556 A1 | 1/2016 | Perera | |

FOREIGN PATENT DOCUMENTS

| | | |
|---|---|---|
| DE | 102008037697 A1 | 2/2010 |
| EP | 2349092 B1 | 1/2017 |
| NL | 2009934 C | 6/2014 |
| RU | 2538633 C2 | 1/2015 |
| WO | 9715253 A1 | 5/1997 |
| WO | 9726841 A2 | 7/1997 |
| WO | 2008014260 A1 | 1/2008 |

OTHER PUBLICATIONS

Examination Report issued in AU2018274877, which is a counterpart hereof, dated Apr. 5, 2019.

Office Action dated Jul. 18, 2019 issued in Australian counterpart application No. 2018274877.

Office Action dated Jun. 27, 2019 issued in Russian counterpart application No. 2018143375/14(072291) and English-language translation thereof.

Office Action and Search Report dated Jul. 27, 2020 issued in Chinese counterpart application No. CN 201811496986.0 and English-language translation thereof.

* cited by examiner

MALE FORM AS AN ATTACHMENT ELEMENT FOR AN INJECTOR, AND INJECTOR FOR IMPLANTING AN INTRAOCULAR LENS IN AN EYE

TECHNICAL FIELD

The invention relates to a male form, which is configured as an attachment element for an injector. The injector is configured to implant an intraocular lens in an eye. Furthermore, the invention also relates to such an injector having a male form.

BACKGROUND

Intraocular lenses are used as implants in an eye and replace the natural lens or to provide refractive correction in a phakic eye (e.g., implantable contact lenses). To this end, injectors are provided, which have a plunger which is guided in an injector tube. Formed at the front end of the injector tube is a receiving space for the intraocular lens, it being possible for this receiving space to be formed in a separate cassette which can be introduced into a frame of the injector tube. Provision can also be made for the receiving space to be formed integrally in the injector tube. Furthermore, an injector tip is formed in a manner adjoining the receiving space toward the front, the injector tip having a guide channel through which the intraocular lens is pushed, after being ejected from the receiving space, and emerges in a folded state at the front and is inserted into the eye. The front side of the tip is introduced directly into the eye.

In known injectors, it is conventional for an injector tip to narrow from the proximal end of the injector tube to a distal front outlet end, from which the intraocular lens is then ejected. The internal volume of the injector tip therefore decreases as far as the outlet end. In this injector tip, an intraocular lens is folded.

Since, during this ejection movement, an ejection element also has to plunge axially into this injector tip, it is known to provide a male form portion as an attachment element on the front end of the plunger. Such an attachment element is known from EP 2 349 092 B1. The attachment element, which is referred to as a male form portion therein, is made of a deformable material, in particular of silicone. The configuration therein is such that the plunger plunges axially into the male form portion at the rear end of the male form portion as seen in the axial direction.

At the front end, in the axial direction, of the male form portion, which is configured in that case as a cylinder, it is possible, in one embodiment, for a hollow cylindrical blind hole to be formed. At the front side of the male form portion, the blind hole is configured in an open manner. In one embodiment, the blind hole is completely filled with a filling material which is different than the silicone material of the male form portion. The filling material is in particular a rigid foam. The additional filling material in turn forms, at the front, a completely coherent and planar surface of the male form portion. As is also specified therein, the filling material counteracts any deformation of that region of the male form portion that has the blind hole.

As a result, the deformation of the male form portion in the front region in a direction perpendicular to a longitudinal axis is limited, however. This then also means that the male form portion is deformed upon being introduced into the narrowing receiving volume of the injector tip, but that, in this regard, relatively large axial pushing forces have to be exerted on the plunger.

Furthermore, EP 2 349 092 B1 mentions a further exemplary embodiment, in which the forwardly open blind hole remains as a cavity or empty space and is not filled with an additional, different material. However, in such an embodiment, an unforeseeable radial deformation is the result. It is therefore not foreseeable to what extent and at which point the region, configured as a tubular portion, of the male form portion will deform. This can in turn have the result that the intraocular lens to be brought into contact with the male form portion no longer comes into contact as desired, and in this connection, an undesired folding operation can occur in the injector tip of the injector. Furthermore, EP 2 349 092 B1 also mentions, with regard to the exemplary embodiment, that, on account of the forces that occur, the wall of the injector, in particular the injector tip, has to be relatively thick in order not to split or to burst on account of the radially outwardly acting forces which can then occur upon axial displacement in the narrowed portion of the injector tip.

In this further exemplary embodiment in the related art, the hollow cylinder is thus configured as a blind hole and therefore completely surrounded in the circumferential direction about the longitudinal axis of the male form portion. The boundary wall, or the front boundary edge, of the blind hole is configured concentrically with the boundary wall, or boundary edge, of the front side of the male form portion. Precisely this configuration brings about the unforeseeable and possible undesired collapse of the front region of the male form portion in a direction perpendicular to the longitudinal axis of the male form portion.

SUMMARY

It is an object of the present disclosure to create a male form for an injector, the male form having an improved deformation behavior. Furthermore, it is an object to create an injector which has such a male form.

One aspect of the diclosure relates to a male form for an injector. The injector is configured to implant an intraocular lens in an eye. The male form is configured as an attachment element for the injector. This means that the male form can be attached to a front end of a plunger of the injector. The male form comprises an elongate carrier part. Furthermore, the male form comprises a front part which is arranged at one end of the carrier part. In the axial direction of the male form, this front part is arranged at a front end of the carrier part. The front end is the end which faces an injector tip of the injector when the male form is arranged in the injector. The front part comprises a front side. This front side faces away from the carrier part. At least the front part is made of an elastically deformable material. This deformable material is compressible at least in the direction of a longitudinal axis of the male form. Preferably, the material is also compressible transversely to the longitudinal axis of the male form. The front side comprises a first boundary side, or first peripheral side, and an opposite second boundary side, or second peripheral side. This means that the surface of this front side is bounded by these two opposite peripheral sides.

Furthermore, the male form comprises at least one elongate indentation which is formed in the front part and which is open at the front side. This means that the indentation in the front part opens toward the front side. The indentation extends, with regard to its orientation along the longitudinal axis of this indentation, between the two peripheral sides and leads out at the peripheral sides.

As a result of such a configuration of a male form, a determinable deformation capability is created for the male form at its front end. As a result of such a foreseeable deformation direction and type of deformation, the effort that is necessary in order to be able to displace the plunger with the male form axially in the injector, in particular then in a narrowing injector tip, is reduced. As a result, it is then also easier for medical personnel to handle the injector. The medical personnel can have a particularly steady hand on implanting the intraocular lens. Trembling of the injector, which may occur on account of a greater effort required by the medical personnel on displacing the plunger in the injector, is avoided here. This also improves the implanting of the intraocular lens in the eye. In addition, deformation of the male form reduces the radial forces exerted by the male form on the wall of the tip through which the lens travels during delivery of the eye.

The indentation is understood to be, in particular, a recess or material cutout in the male form, the recess or cutout extending with its longitudinal axis perpendicular to a longitudinal axis of the plunger. The indentation is configured in particular in a track-like or channel-like manner. The indentation starts in particular directly at a peripheral side of the front side of the front part and extends without interruption as far as an opposite further peripheral side of the front side, the indentation also ending directly at this opposite peripheral side. An indentation is bounded in particular by opposite wall regions elongated in a direction of a longitudinal axis of the indentation which are typically not arranged parallel to one another. In particular, these wall regions are oriented at an angle to one another, more particularly obliquely with respect to one another. Typically, these wall regions are oriented obliquely with respect to one another starting from an opening of the indentation at the front side as far as a bottom of the indentation.

In an advantageous embodiment, provision is made for the elongate indentation to be configured in a rectilinear manner. It thus extends as a straight line without interruption between the peripheral sides. Such a configuration is easy to produce and can furthermore be designed in a dimensionally precise manner. This again promotes the abovementioned advantages in terms of a particularly precisely determinable deformation direction of the front part when force is applied, in particular, when force is applied with a force component acting perpendicularly to the longitudinal axis of the male form.

Provision is typically made for the indentation to be configured in an open manner at its opposite ends at the peripheral sides. As a result of this configuration, this elongate indentation is destabilized in a defined manner at the two opposite ends, such that the desired, targeted, and directed deformation of the front part of the male form is improved even further.

Typically, the front part is configured in a plate-like manner. It represents in particular a front-side shield of the male form. As a result of this specific shaping and exposed position of such a subcomponent of the male form, the configuration of a dimensionally specific and locally individually designed indentation is also improved. The front part is preferably configured in the manner of a knight's shield.

Provision is typically made for the indentation to divide the front part, at least at the front side, into at least two front-side segments and for the indentation to form a predetermined bending point for the front part. This predetermined bending point is thus specified in a defined manner, such that when a force is applied to a peripheral side of the front part. These front-side segments are bent along the predetermined bending point such that they move toward one another, and radially collapse virtually in a direction perpendicular to the longitudinal axis of the male form. This is a further exemplary embodiment, which allows the defined deformation behavior of this male form, in particular, of the front part newly created here. This results in a further particular advantage in order to achieve reduced-force displacement of the plunger in the injector tube, in particular, when the male form enters the narrowing injector tip. Furthermore, such a configuration also allows more continuous displacement of the male form, in particular in the injector tip. The action of the male form on the intraocular lens, with which direct contact is made by the front part, in particular, indentation, is very metered as a result, such that undesired force effects on the intraocular lens can likewise be avoided. As a result of this configuration of the male form as such and also the deformation behavior thereof, in particular on entering the injector tip of the injector, the folding behavior of the intraocular lens in the injector tip is very defined and supported as desired.

Provision is preferably made for the elongate indentation to have a V-shape in a cross-section perpendicular to a longitudinal axis of the indentation. This is a particularly advantageous embodiment, since, in this way, the geometry of this indentation is presented with a maximum opening width at the mouth of the V-shape, such that the moving toward one another, i.e., collapsing of the front part is improved. In particular, this then also allows a collapsing movement which does not just take place in a direction perpendicular to the longitudinal axis of the male form, but a component of the collapsing movement which is oriented axially is also present in this regard. Furthermore, this V-shape creates a geometry which also forms a particularly noteworthy predetermined bending point. This is because the bottom of the V-shape, which is usually in the form of a point and thus represents only a sharp edge or line, then also creates a very precise predetermined bending line. The particularly advantageous and precise deformation is achieved as a result. In particular the start of the deformation behavior and then also the type of deformation and deformation direction are allowed in a particularly precise manner by this configuration.

In an alternative exemplary embodiment, the indentation can also be concave or U-shaped or box-shaped, however, in a cross-section perpendicular to a longitudinal axis of the indentation.

In an advantageous embodiment, the indentation has a depth of between 0.4 mm and 1.5 mm, measured perpendicularly to the longitudinal axis. As a result of such a configuration, the indentation is advantageously designed, since the stability of the male form is not excessively weakened in an undesired manner, but the indentation nevertheless also creates a situation in which the front part can collapse in a defined and reliable manner, or can deform in a defined manner, with its front-part segments that are preferably then formed.

Provision is typically made for the indentation to have a bottom line which is the deepest point of the indentation, this bottom line being shorter, as seen in the direction of the longitudinal axis of the indentation, at at least one end of the indentation than a boundary, formed on the front side of the front part, of the indentation. In this way, too, the deformation behavior is advantageously supported. Such a configuration is provided in particular when the carrier part has a portion which opens out directly at this front part or at a rear side of the front part, this portion of the carrier part being formed in a conical manner or tapering.

The indentation is formed in a manner open toward the front and as a material-free empty space or clearance. In the provided state of the male form, the indentation is therefore not filled with an additional material, in particular, not with a different material than the front part and the carrier part.

In particular, provision is made for the front part, as seen perpendicularly to the longitudinal axis of the male form, to be formed with a bead-like protuberance with respect to the carrier part adjoining the front part to the rear. This means that the front part protrudes outwardly in the radial direction with respect to the longitudinal axis of the male form, or extends farther outward than that portion of the carrier part that opens out directly at the rear side of the front part. As a result of such a collar or corresponding bead, the front part is defined as a separate object part. Furthermore, as a result of this bead, which is formed in a relatively thin manner in the axial direction and in particular has an axial extent of between 0.5 mm and 1 mm in this regard, the front part is also designed to be in turn more deformable than if such a protuberance were not present. Since the male form bears against the inner side, in particular the injector tip, correspondingly reduced contact is formed by this configuration, in which only the periphery of this bead of the front part then butts against the inner side. On account of the specific material configuration of the front part made of an elastically deformable material and this geometric specification of the front part, the deformation behavior of the male form at the front end is then in turn also improved. Compared with embodiments in which such a protuberance is not present, the easier deformation and thus radial collapse is then allowed more precisely in terms of direction.

Provision is preferably made for the male form to be formed in one piece. In particular, the male form is made of a material with a Shore hardness of between 35 and 45 Shore A.

In a further advantageous embodiment, provision may be made for the front part to have at least two indentations which are separate and each separately have an individual geometry. The two indentations can be configured in a linear manner and in particular also extend in a rectilinear manner. Thus, the indentations can then be oriented at a particular angle to one another. In particular, in this case, an angle of 90° can be formed, such that the system of the two indentations forms a cross.

The depth, measured in the direction of the longitudinal axis of the male form, of the indentation can be greater or less than or the same as the thickness, measured in the direction of this longitudinal axis of the male form, of the front part. Thus, in one embodiment, provision may also be made for the depth of the indentation to extend through the entire front part and also to extend into the carrier part that opens out at the rear side of the front part.

The at least one indentation is also a defined direction indicator for the collapsing direction of the front part in a direction perpendicular to the longitudinal axis of the male form.

A further independent aspect of the disclosure relates to a male form for an injector. The injector is configured to implant an intraocular lens in an eye. The male form is configured as an attachment element for the injector. This means that the male form can be attached to a front end of a plunger of the injector. The male form comprises an elongate carrier part. Furthermore, the male form comprises a front part which is arranged at one end of the carrier part. In the axial direction of the male form, this front part is arranged at a front end of the carrier part. The front end is the end which faces an injector tip of the injector when the male form is arranged in the injector. The front part comprises a front side. This front side faces away from the carrier part. At least the front part is made of an elastically deformable material. This deformable material is compressible in the direction of a longitudinal axis of the male form. The front side comprises a first boundary side, or first peripheral side, and an opposite second boundary side, or second peripheral side. This means that the surface of this front side is bounded by these two opposite peripheral sides. The male form comprises at least one rectilinear indentation which is formed in the front part and is open at the front side. The indentation extends between the two peripheral sides of the front part and leads out at the peripheral sides. The indentation is configured in an open manner at its two opposite ends at these peripheral sides. Thus, as seen in the direction of the longitudinal axis of the male form, the indentation is open toward the front and is likewise configured in an open manner at the opposite ends of the channel-like indentation in the direction perpendicular to this longitudinal axis of the male form. This also means that, as seen in the direction of the longitudinal axis of the indentation, the indentation is open at its ends.

Another independent aspect of the disclosure relates to a male form for an injector. The injector is configured to implant an intraocular lens in an eye. The male form is configured as an attachment element for the injector. This means that the male form can be attached to a front end of a plunger of the injector. The male form comprises an elongate carrier part. Furthermore, the male form comprises a front part which is arranged at one end of the carrier part. In the axial direction of the male form, this front part is arranged at a front end of the carrier part. The front end is the end which faces an injector tip of the injector when the male form is arranged in the injector. The front part comprises a front side. This front side faces away from the carrier part. At least the front part is made of an elastically deformable material. This deformable material is compressible in the direction of a longitudinal axis of the male form. The front side has a first boundary side, or first peripheral side, and an opposite second boundary side, or second peripheral side. This means that the surface of this front side is bounded by these two opposite peripheral sides.

The male form comprises at least one indentation which is formed in the front part, this indentation being open at the front side. As a result of the indentation, the front part is divided into at least two front-part segments at least at the front side. The indentation forms a predetermined bending point such that, when a force is applied to a peripheral side of the front part, these front-part segments are bent along the predetermined bending point such that they move toward one another.

Exemplary embodiments of the respective independent aspects of the male forms, as have been mentioned, should be considered advantageous embodiments of the respective other aspects of a male form.

Furthermore, the disclosure also generally relates to an injector for implanting an intraocular lens in an eye. The injector comprises a male form which can be configured as per the exemplary embodiments set out above. The male form is a front-side attachment element for a plunger of the injector.

A further aspect of the disclosure relates to an injector for implanting an intraocular lens in an eye. The injector comprises an injector tube and an injector tip. Furthermore, the injector comprises a plunger which is arranged in a displaceable manner in the injector tube. Moreover, the injector comprises a male form, which is arranged as an attachment element at a front end of the plunger. The male form represents a separate component from the plunger. The male form is arranged in the injector tube in such a way that the male form moves into the injector tip when the plunger is displaced axially in the injector tube. The injector tip is configured with a narrowed internal volume. This means that, starting from the end at which it opens out rearwardly at the injector tube, the male form narrows, in particular narrows continuously, as far as a front end which faces away from the injector tube. Preferably, a loading chamber, into which the intraocular lens to be implanted can be introduced, is formed in the injector. For example, the injector can have an insertable cassette for this purpose, which is insertable into this loading chamber.

The male form comprises an elongate carrier part. Furthermore, the male form comprises a front part which is arranged at one end of the carrier part. In the axial direction of the male form, this front part is arranged at a front end of the carrier part. The front end is the end which faces an injector tip of the injector when the male form is arranged in the injector. The front part comprises a front side. This front side faces away from the carrier part. At least the front part is made of an elastically deformable material. This deformable material is compressible at least in the direction of a longitudinal axis of the male form. Typically, the material is also compressible transversely to the longitudinal axis of the male form. The front side has a first boundary side, or first peripheral side, and an opposite second boundary side, or second peripheral side. This means that the surface of this front side is bounded by these two opposite peripheral sides.

Furthermore, the male form comprises at least one elongate indentation which is formed in the front part and which is open at the front side. This means that the indentation in the front part opens toward the front side. The indentation extends, with regard to its orientation along the longitudinal axis of this indentation, between the two peripheral sides and opens out at the peripheral sides.

Further features of the disclosure can be gathered from the claims, the figures and the description of the figures. The features and combinations of features mentioned above in the description, and the features and combinations of features mentioned below in the description of the figures and/or shown in isolation in the figures are usable not only in the combination specified in each case but also in other combinations, without departing from the scope of the invention. Exemplary embodiments of the disclosure, which are not explicitly shown and explained in the figures, but are apparent from and are able to be produced by separate combinations of features from the exemplary embodiments explained, should thus also be considered to be included and disclosed. Exemplary embodiments and combinations of features should also be considered to be disclosed which therefore do not exhibit all the features of an originally formulated independent claim. Furthermore, embodiments and combinations of features which go beyond or differ from the combinations of features set out in the back-references of the claims, should be considered to be disclosed, in particular by the embodiments set out above.

The specific values, set out in the documents, of parameters and data relating to relationships of parameters or parameter values for defining exemplary embodiments of the eye lens should also be considered to be also included in the scope of the disclosure in the context of deviations, for example on account of measuring errors, system errors, DIN tolerances etc., and so explanations which relate to substantially corresponding values and data should be understood as being included therein.

BRIEF DESCRIPTION OF THE DRAWINGS

Exemplary embodiments of the disclosure are explained in more detail in the following text with reference to schematic drawings, in which.

DETAILED DESCRIPTION OF EXEMPLARY EMBODIMENTS

In the figures, identical or functionally identical elements are provided with the same reference signs.

Figure 1:
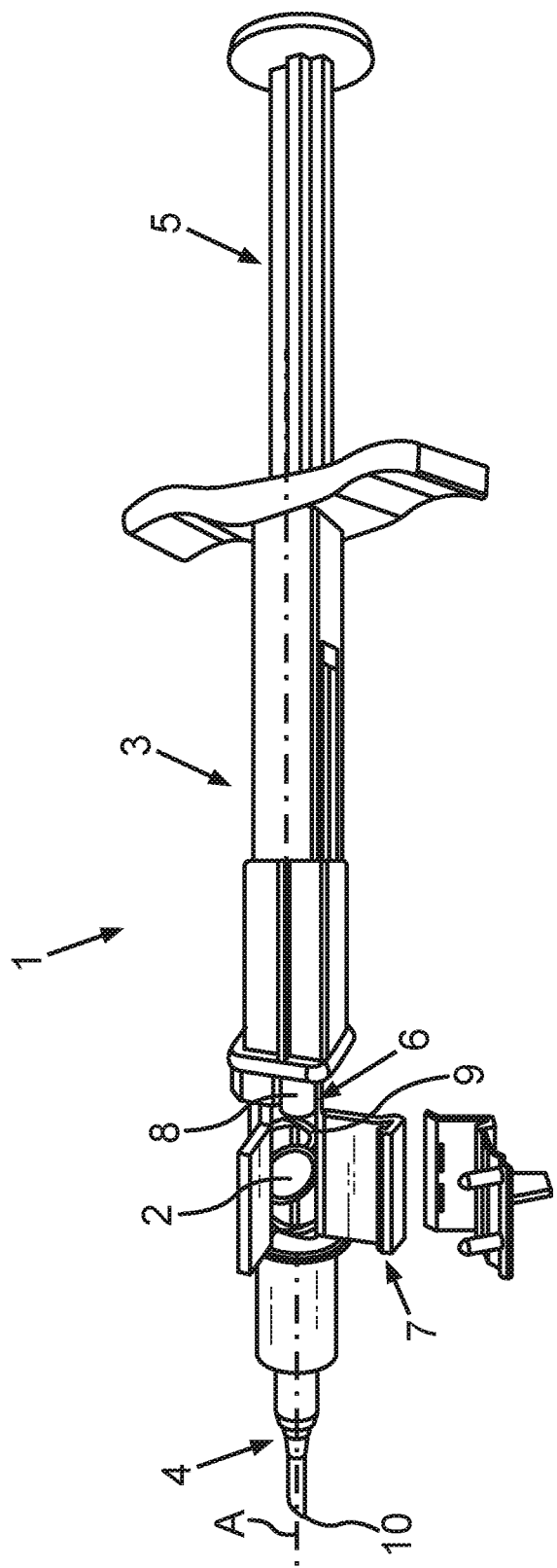
FIG. 1 shows a perspective illustration of an exemplary embodiment of an injector.

FIG. 1 shows an illustration of an exemplary embodiment of an injector 1. The injector 1 is configured to implant an intraocular lens 2 in an eye.

The injector 1 is configured in the form of a syringe. The injector 1 has an injector tube 3. Furthermore, the injector 1 has an injector tip 4. The injector tip 4 adjoins the injector tube 3 at a front end in the direction of the longitudinal axis A of the injector 1. A plunger 5 of the injector 1 is mounted in an axially displaceable manner in the interior of the injector tube 3. The injector tube 3 furthermore has a loading chamber 6 into which the intraocular lens 2 can be introduced. The loading chamber 6 is preferably configured such that a separate cassette 7, in which the intraocular lens 2 is arranged, can be inserted into the loading chamber 6. Furthermore, the injector 1 has a male form 8. The male form 8 is configured as an attachment element on a front end of the plunger 5. The attachment element 8 is also designed as a damper and is preferably made entirely of an elastically deformable material. The male form 8 is a separate component from the plunger 5.

When the inherently rigid plunger 5 is displaced axially, the attached male form 8 then comes into contact with the intraocular lens 2, in particular at a haptic 9 of the intraocular lens 2. As a result of further axial displacement of the plunger 5, the male form 8 pushes the intraocular lens 2 out of the cassette 7 and into the injector tip 4. The injector tip 4, as can also be seen in FIG. 1, is configured with a narrowing receiving volume. In the injector tip 4, the intraocular lens 2 is folded and then passes in a folded state out of the injector tip 4 at a front end 10 and into the eye.

Figure 2:
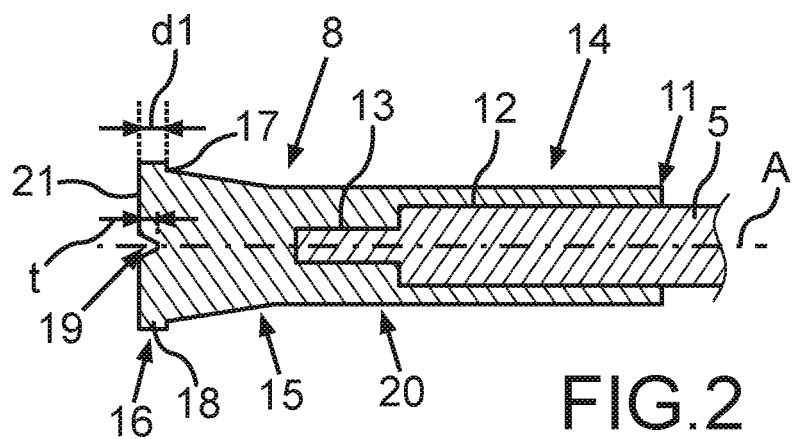
FIG. 2 shows a sectional illustration through a subregion of the injector, in which an exemplary embodiment of a male form is shown, which is arranged as an attachment element at a front end of the plunger of the injector.

FIG. 2 shows a sectional illustration of a subregion of the plunger 5 and the male form 8. As can be seen here, the plunger 5 plunges into the male form 8 in the axial direction via a rear end 11. In this connection, the male form 8 has a first receiving region 12 and a second receiving region 13 adjoining toward the front in the axial direction. These two receiving regions 12 and 13 have different radial dimensions. The rear first receiving region 12 has a larger dimension in the radial direction and thus perpendicularly to the longitudinal axis A than the front second receiving region 13.

Preferably, the male form 8 is configured in one piece. The male form 8 is made at least regionally, in particular entirely, of an elastically deformable material in an advantageous embodiment. In particular, the male form 8 is made of silicone. Typically, the elastically deformable material of the male form 8 has a Shore hardness of between 35 and 45 Shore A, in particular between 38 and 42 Shore A.

In the exemplary embodiment shown here, the rod-like male form 8 is formed with a rear male form portion 14 which is designed in a tubular manner and has an identical radial diameter along its entire axial length. Furthermore, the male form 8 has a front second male form portion 15. This second male form portion 15 directly adjoins the first male form portion 14 axially. The second male form portion 15 is designed in a conical manner. This means that it widens starting from its rear end, at which it opens out at a front end of the first male form portion 14. The male form 8 furthermore has a front part 16. The front part 16 represents a plate-like front end part. The front part 16 is also formed as a front shield. The second male form portion 15 directly adjoins a rear side 17 of this front part 16.

The front part 16 preferably has a thickness d1 which is measured in the direction of the longitudinal axis A and is preferably between 0.6 mm and 1 mm.

Furthermore, it can be seen from the illustration in FIG. 2 that the front part 16 extends further outward, as seen in the direction perpendicular to the longitudinal axis A, with a protuberance 18, than the adjoining second male form part, or the second male form portion 15. In particular, the protuberance 18, configured as a bead, is in the form of an encircling collar. This collar is interrupted, in an exemplary embodiment, only at the points at which an indentation 19 opens out at the periphery.

The two male form portions 14 and 15 in the exemplary embodiment form a carrier part 20 of the male form 8. A male form 8 thus has a carrier part 20 and the front part 16, which is formed integrally therewith and arranged at the end side.

Figure 3:
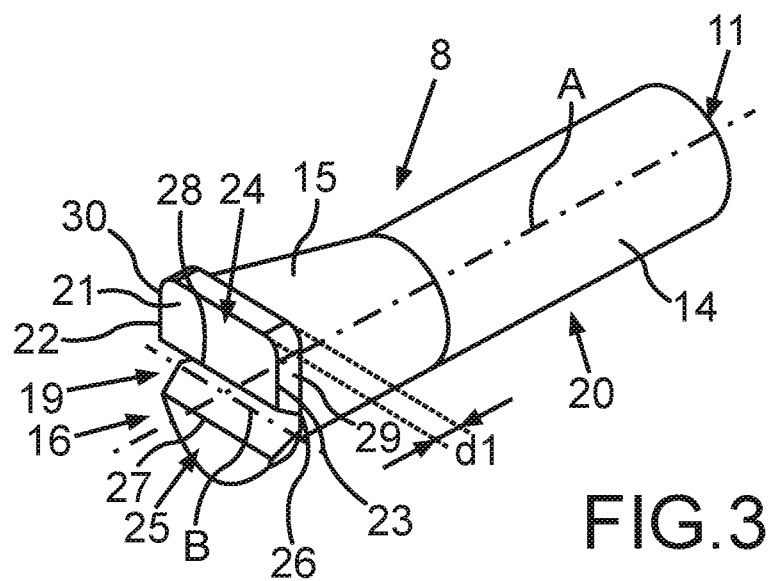
FIG. 3 shows a perspective illustration of one exemplary embodiment of a male form according to the invention.

FIG. 3 shows the exemplary embodiment of the male form 8, as was explained in FIG. 2. The front part 16 has a front side 21 which faces away from the carrier part 20 and faces the injector tip 4 in the state of the male form 8 inserted into the injector tube 3.

Formed in the front part 16 is at least one indentation 19. This indentation 19 is preferably elongate, in particular designed in a linear manner, and represents in particular a trench which is configured without interruption. The indentation 19 extends, in the exemplary embodiment shown, between a first peripheral side 22 and an opposite second peripheral side 23. The two peripheral sides 22 and 23 bound the surface of the front side 21. The indentation 19 thus opens out with its opposite ends directly at the peripheral sides 22 and 23. The indentation 19 is open toward the front as seen in the direction of the longitudinal axis A. The indentation 19 has a longitudinal axis B which is oriented perpendicularly to the longitudinal axis A in the exemplary embodiment shown. At the opposite ends of the indentation 19, which are located opposite one another in the direction of the longitudinal axis B thereof, the indentation 19 is likewise typically formed in an open manner here. This is shown in FIG. 3. As a result, as can be seen, the peripheral sides 22 and 23 are interrupted. The indentation 19 has a depth t which is measured in the direction of the longitudinal axis A. This depth t (FIG. 2) may be greater than, the same as or less than the thickness d1. In the exemplary embodiment shown in FIG. 3, this depth t is less than or equal to the thickness d1. The depth t may be between 0.4 mm and 1.5 mm.

Furthermore, provision is made, in the exemplary embodiment shown, for the shape of the indentation 19 to be V-shaped in a cross-sectional plane which is oriented perpendicularly to the longitudinal axis B. Wall regions of the indentation 19 are thus oriented obliquely with respect to one another. The indentation 19 forms a predetermined bending point in particular for the front part 16. The indentation 19 forms, in its specific geometry, a predetermined bending trench. As a result of this indentation 19, a weakening path of the material is thus also formed. As a result of this geometrically and locally defined configuration of the indentation 19, a defined weakening path of the front part 16 is also specified. By way of this weakening path, a weakening line for weakening the dimensional stability of the front part 16 is formed, such that a collapsing direction specified in a defined manner for the front part 16 is specified. As a result of the indentation 19, the front part 16 is divided into two front-part segments 24 and 25. These front-part segments 24 and 25 are also already present and specified in a defined manner when the male form 8 is in its basic state and thus in its non-deformed state.

In particular as a result of the V-shape already set out above, this predetermined bending point is formed as a line 26, with a predetermined bending line that is then also configured in a very precise manner. The line 26 can also be referred to as an edge here. The defined deformation, in particular about this rectilinear predetermined bending line, is allowed in a particularly advantageous manner as a result. By contrast, the indentation 19 is likewise bounded, at its open end at the front side 21, by boundary lines or boundary edges 27 and 28. These are configured in a rectilinear manner in the exemplary embodiment.

In a further exemplary embodiment, provision can be made for these boundary edges 27 and 28 also to be able to be non-rectilinear and for example, in particular each, to have a saw tooth shape or a wave shape, in particular a sine wave shape.

Figure 4:
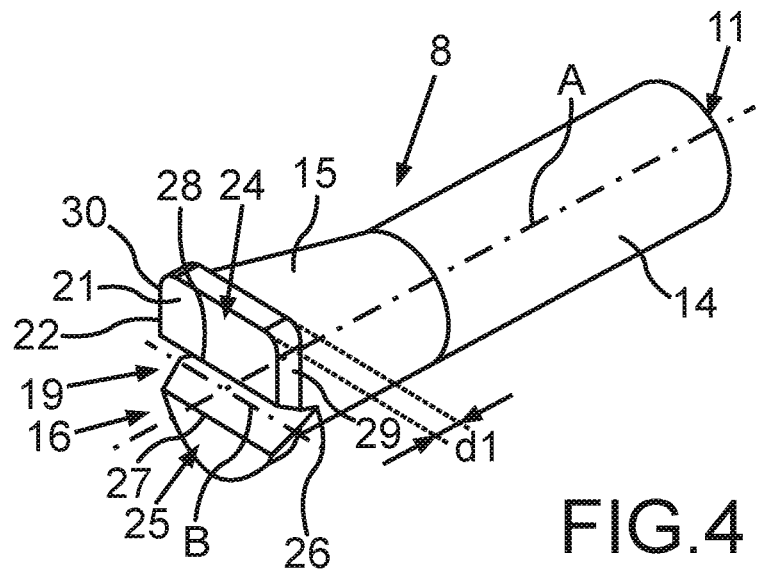
FIG. 4 shows a perspective illustration of a further exemplary embodiment of a male form according to the invention.

FIG. 4 shows a perspective illustration of a further exemplary embodiment of a male form 8. In contrast to the embodiment according to FIG. 3, provision is made here for this depth t to be greater than the thickness d1. As a result, in this embodiment, the indentation 19 also extends into the carrier part 20 formed therebehind, in particular into the second male form portion 15.

Figure 5:
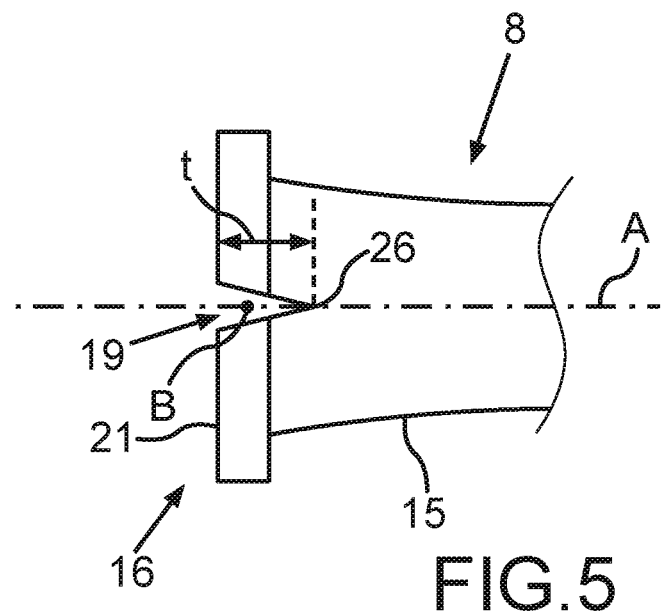
FIG. 5 shows a side view of a subregion of the male form according to FIG. 3.

FIG. 5 shows a side view of the male form according to FIG. 4, but only in the front section with the front part 16 and the second male form portion 15. The geometry of the indentation 19 and the depth t in the direction of the longitudinal axis A are shown here.

Figure 6:
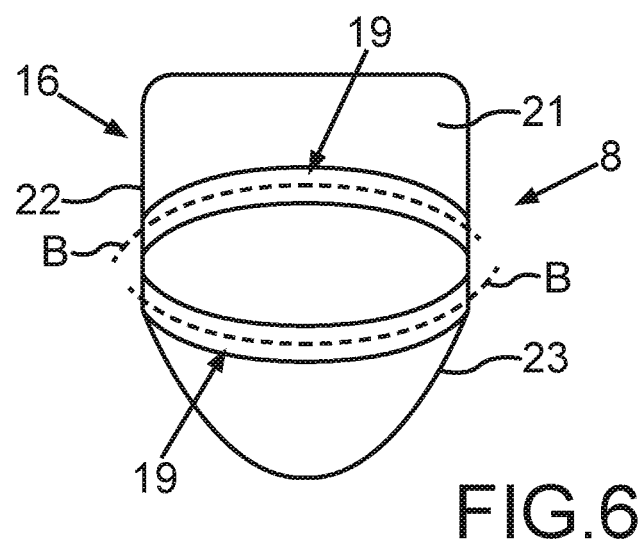
FIG. 6 shows a front view of a front part of a further exemplary embodiment of a male form.

FIG. 6 shows a schematic illustration of a further exemplary embodiment of a male form 8, only the front part 16 with a view of the front side 21 being illustrated here. In this example, two indentations 19 are configured as in each case separate, spaced-apart indentations 19 that are not in contact with one another. The indentations 19 in this case likewise extend without interruption over the entire width of the front side 21 and open out at the peripheral sides 22 and 23 of the front side 21. Here too, the elongate indentations 19 are configured in an open manner at their opposite ends at which they open out at the peripheral sides 22 and 23. In this embodiment, the indentations 19 are not configured in an entirely rectilinear manner but in particular in a curved, in particular continuously curved manner. As a result, the indentations 19 are designed in an arcuate manner here.

Figure 7:
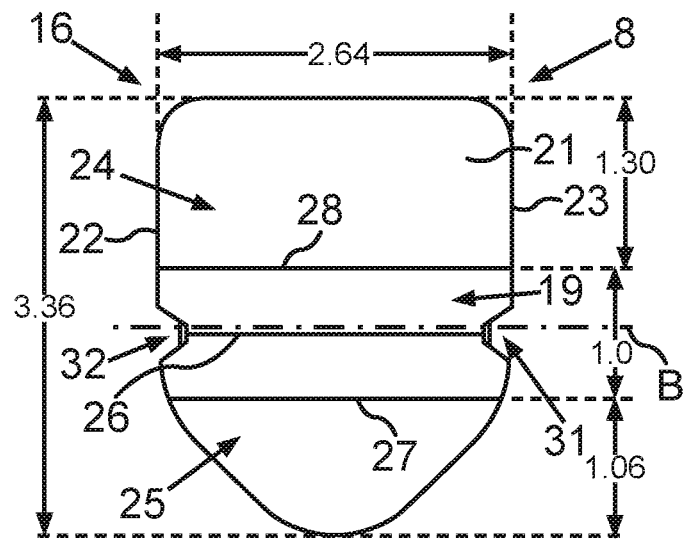
FIG. 7 shows a front view of a front side of a front part of the male form according to FIG. 2 and FIG. 3.

FIG. 7 shows a front view of the male form 8 according to FIG. 3. Exemplary dimensions in millimeters, which should not be understood as being limiting in any way, are likewise specified.

The deepest point of the indentation 19 is, in the geometry explained here as an example, the tip of the V-shape, which is characterized by the line 26. This line 26 thus also represents a bottom line of the indentation 19.

As can be seen in FIG. 7, this line 26 extends along the longitudinal axis B of the indentation 19 along a length which is shorter than the lengths of the upper boundary edges 27 and 28. In particular, provision can be made in this connection for the peripheral faces 29 and 30 of the front part 16 not to extend with their planes parallel to the section plane in FIG. 2, but to be oriented at least partially obliquely thereto. This results in a front side image, as is shown in FIG. 7, in which this indentation 19 is not only formed in an open manner at its opposite ends, but also has further peripheral notches 31 and 32 in this projection view according to FIG. 7.

Figure 8:
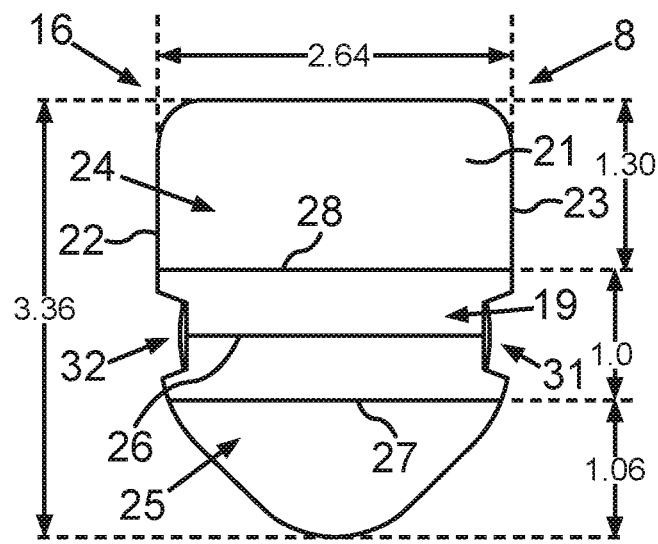
FIG. 8 shows a front view of the front side of a front part of the male form according to FIG. 4.

FIG. 8 shows the corresponding illustration as in FIG. 7 but for the exemplary embodiment of the male form 8 according to FIG. 4. In this regard, the indentations 31 and 32 are designed in a different way and are larger in front view.

Figure 9:
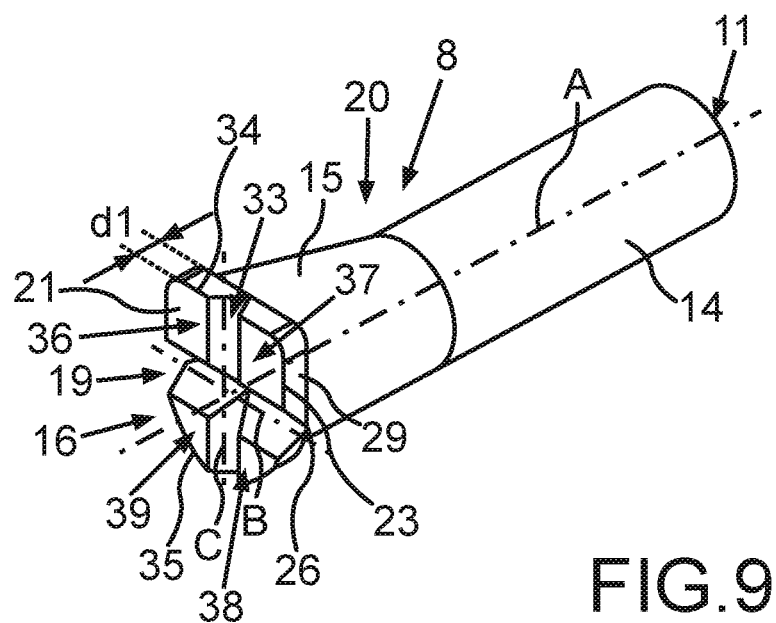
FIG. 9 shows a perspective illustration of a further exemplary embodiment of a male form.

FIG. 9 shows a perspective illustration of a further exemplary embodiment of a male form 8. In this embodiment, in contrast to the illustration in the previous figures, a first indentation 19 and a second indentation 33 are formed. With regard to its geometry and orientation, the first indentation 19 can be designed preferably as in the embodiments in FIGS. 2 to 8. The further indentation 33, separate therefrom, is arranged at an angle, in particular 90°, thereto in the exemplary embodiment shown. This forms a system of indentations 19, 33 which forms a cross. The further indentation 33 has a longitudinal axis C which is oriented both perpendicularly to the longitudinal axis B and perpendicularly to the longitudinal axis A. The second indentation 33 is likewise configured as an elongate indentation 33, which extends preferably in a rectilinear manner between further opposite peripheral sides 34 and 35 of the front side 21. In this embodiment, the depths, measured in the direction of the longitudinal axis A, of the indentations 19 and 33 are between 0.4 mm and 0.6 mm, preferably 0.5 mm. In an advantageous embodiment, the cross-sectional shape of the further indentation 33 is likewise V-shaped in a plane perpendicular to its longitudinal axis C. As a result of this cross, the front part 16 and in particular the front side 21 has four front-part segments 36, 37, 38 and 39 here. The further indentation 33 is also configured in an open manner at its opposite ends as seen in the direction of the longitudinal axis C and opens out directly at the peripheral sides 34 and 35.

In an embodiment in which the indentation 19 extends at most down to a depth t which corresponds to the thickness d1, it is also possible for the end-side further notches 31 and 32 not to be present, in particular when the peripheral faces 29 and 30 are oriented parallel to a cross-sectional plane through which the longitudinal axis A extends.

Figure 10:
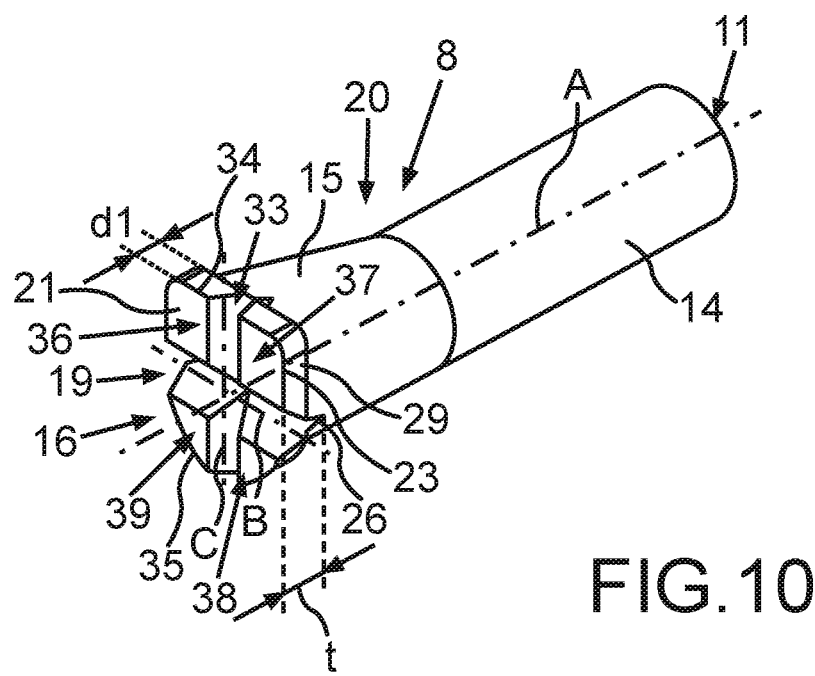
FIG. 10 shows a perspective illustration of a further exemplary embodiment of a male form.

FIG. 10 shows a further exemplary embodiment of a male form 8. In contrast to the illustration according to FIG. 9, provision is made here for the indentations 19 and 33 to extend over a depth which is greater than the thickness d1. Therefore, in this exemplary embodiment, the indentations 19 and 33 extend right into the carrier part 20, in particular right into the second male form portion 15. In this embodiment, the depth t of the two indentations 19 and 33 can be between 0.30 mm and 1.2 mm, in particular 0.80 mm.

Figure 11:
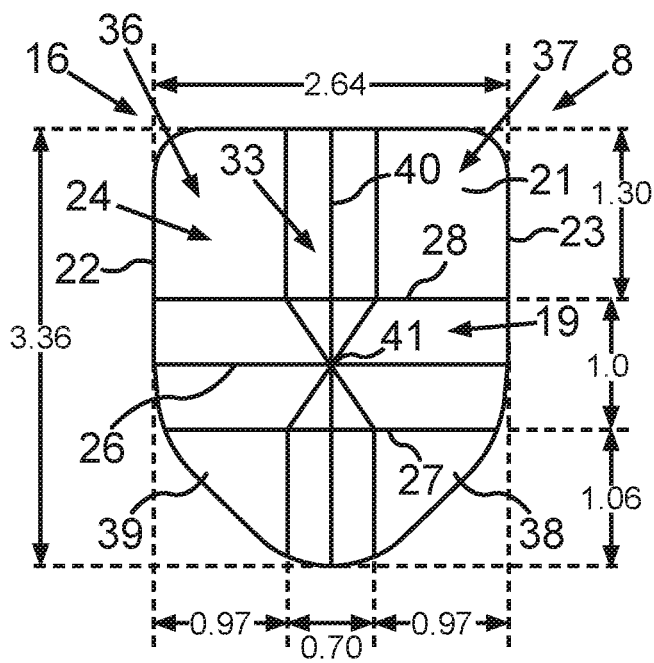
FIG. 11 shows a front view of a front side of a front part of the male form according to FIG. 9.

FIG. 11 in turn shows a front view of the front side 21 of the male form 8 according to FIG. 9. The lines 26 and 40, representing bottom lines, of the indentations 19 and 33 are in turn in particular rectilinear here and intersect at a point 41. This point 41 can also be referred to as a predetermined bending point. As can be seen in FIG. 11, the indentations 19 and 33 do not have end-side further notches here, as are shown by way of example by the notches 31 and 32 in FIG. 7 and FIG. 8.

Figure 12:
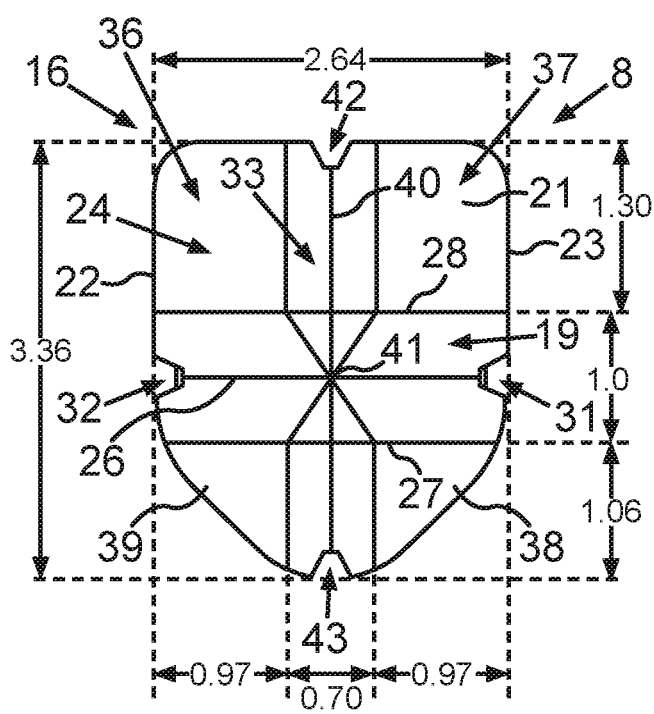
FIG. 12 shows a front view of a front side of a front part of the male form according to FIG. 9.

FIG. 12 shows a front view of the male form 8 corresponding to the illustration in FIG. 11. It can be seen here that, in particular on account of the depth t, peripheral notches 31 and 32 of the indentation 18 are present and the indentation 33 also has peripheral notches 42, 43.

In all of the exemplary embodiments, provision is made for the indentations 19, 33 to be configured without a material filling and thus also for an air space or clearance to be formed by the indentations 19, 33 in the finished, provided state of the male form 8.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

The invention claimed is:

1. A male form configured as an attachment element for an injector, the injector being configured to implant an intraocular lens in an eye, the male form comprising:
   an elongate carrier part,
   a front part arranged at one end of the elongate carrier part,
   the front part having a front side and being made of an elastically deformable material, the deformable material being compressible at least in the direction of a longitudinal axis (A) of the male form, and the front side including a first peripheral side and an opposite second peripheral side,
   at least one elongate indentation formed in the front part, being open at the front side, being bounded by a first boundary edge extending between the first peripheral side and the opposite second peripheral side and a second boundary edge, the at least one elongate indentation extending in a direction perpendicular to edges of the first peripheral side and the opposite second peripheral side, the first boundary edge defining a first distance, and the second boundary edge defining a second distance, the at least one elongate indentation extending between the first peripheral side and the opposite second peripheral side and opening out at the first peripheral side and the opposite second peripheral side, the at least one elongate indentation dividing the front part, at least at the front side, into at least two front-part segments, and the at least one elongate indentation forming a predetermined bending point, the front-part segments being bent along the predetermined bending point and moving toward one another when a force is applied to a peripheral side of the front part, and the at least one elongate indentation having a longitudinal axis and including a bottom line defining a third distance of an entire length of the at least one elongate indentation at a deepest point of the at least one elongate indentation in the direction of the longitudinal axis of the at least one elongate indentation, and the third distance being shorter than the first distance and the second distance, wherein the front part has a plate-like shape and a thickness measured in a direction of a longitudinal axis (A) of the male form and an outer periphery, wherein the elongate carrier part has a front portion and a rear portion, wherein the front portion has a conical shape which widens towards the front part defining a maximum diameter at the distal end, wherein the outer periphery of the front part extends beyond the diameter of the distal end of the front portion, and wherein the rear portion has a cylindrical shape.

2. The male form as claimed in claim 1, wherein the at least one elongate indentation is rectilinear.

3. The male form as claimed in claim 1, wherein the at least one elongate indentation is open at opposite ends of the peripheral sides.

4. The male form as claimed in claim 1, wherein the at least one elongate indentation comprises a V-shape in a cross-section perpendicular to a longitudinal axis (B, C) of the at least one elongate indentation.

5. The male form as claimed in claim 1, wherein the at least one elongate indentation is a material-free empty space.

6. The male form as claimed in claim 1, wherein the front part, as seen perpendicularly to the longitudinal axis (A) of the male form, is formed with a bead-like protuberance with respect to the carrier part adjoining the front part to a rear.

7. The male form as claimed in claim 1, wherein the male form is made in one piece of a material with a Shore hardness of between 35 and 45 Shore A.

8. The male form as claimed in claim 1, wherein:
the at least one elongate indentation has a depth, and
the depth of the elongate indentation is larger than the thickness of the front part.

9. An injector for implanting an intraocular lens in an eye, comprising:
an injector tube,
an injector tip,
a plunger being displaceably arranged in the injector tube, and
a male form being arranged as an attachment element at a front end of the plunger, the male form comprising:
an elongate carrier part,
a front part being arranged at one end of the elongate carrier part,
the front part including a front side and being made of an elastically deformable material, the deformable material being compressible at least in the direction of a longitudinal axis (A) of the male form, and the front side having a first peripheral side and an opposite second peripheral side, and
at least one elongate indentation formed in the front part, being open at the front side, being bounded by a first boundary edge extending between the first peripheral side and the opposite second peripheral side and a second boundary edge, the at least one elongate indentation extending in a direction perpendicular to edges of the first peripheral side and the opposite second peripheral side, the first boundary edge defining a first distance, and the second boundary edge defining a second distance, the at least one elongate indentation extending between the first peripheral side and the opposite second peripheral side and opening out at the first peripheral side and the opposite second peripheral side, the at least one elongate indentation dividing the front part, at least at the front side, into at least two front-part segments, and the at least one elongate indentation forming a predetermined bending point, the front-part segments being bent along the predetermined bending point and moving toward one another when a force is applied to a peripheral side of the front part, and the at least one elongate indentation having a longitudinal axis and including a bottom line defining a third distance of an entire length of the at least one elongate indentation at a deepest point of the at least one elongate indentation in the direction of the longitudinal axis of the at least one elongate indentation, and the third distance being shorter than the first distance and the second distance, wherein the front part has a plate-like shape and a thickness measured in a direction of a longitudinal axis (A) of the male form and an outer periphery, wherein the elongate carrier part has a front portion and a rear portion, wherein the front portion has a conical shape which widens towards the front part defining a maximum diameter at the distal end, wherein the outer periphery of the front part extends beyond the diameter of the distal end of the front portion, and wherein the rear portion has a cylindrical shape.

10. The injector as claimed in claim 8, wherein:
the at least one elongate indentation has a depth, and
the depth of the elongate indentation is larger than the thickness of the front part.

* * * * *